United States Patent [19]

Wagner, Jr. et al.

[11] 3,971,271
[45] July 27, 1976

[54] WRENCH FOR SURGICAL USE

[76] Inventors: Frederick William Wagner, Jr., 1650 Amate Drive, Whittier, Calif. 90603; Thomas A. Rickard, 46 Windjammer Court, Long Beach, Calif. 90803

[22] Filed: Aug. 25, 1975

[21] Appl. No.: 607,666

[52] U.S. Cl. .............................................. 81/57.29
[51] Int. Cl.² ........................................ B25B 17/00
[58] Field of Search .............. 81/57.29, 57.3, 57.31, 81/57.14, 58.1, 58.2, 125

[56] References Cited
UNITED STATES PATENTS

| | | | |
|---|---|---|---|
| 1,635,102 | 7/1927 | Watson | 81/125 |
| 3,477,318 | 11/1969 | Batten | 81/57.3 |
| 3,535,960 | 10/1970 | Borries | 81/57.14 |
| 3,602,071 | 8/1971 | Juhasz | 81/57.3 |

*Primary Examiner*—James L. Jones, Jr.
*Attorney, Agent, or Firm*—J. Carroll Baisch

[57] ABSTRACT

A wrench for surgical use including a housing having an extension at the end of which there is a socket member having a slot through the wheel thereof with the socket member aligned with the corresponding slot in the free end of the extension to permit a nut on an extremely threaded rod to pass into the socket. The socket is peripherally toothed for engagement by a pair of worm gears disposed at respective sides of the socket member so that there is always driving engagement between the worm gears and socket member for rotating the socket member. Crank operated gears are exposed in the housing and are connected by drive shafts of the worm gears.

A slidable nut retainer is disposed at each side of the extension and each is provided with a notch for reception of the threaded rod; the parts of the slidable nut retainer at the side of the notches, overlap the nut to prevent it from coming out of the socket. The slidable nut retainer members each have a ridge on the underside adapted to be received in notches at the limits of movement of the slidable nut retaining members.

7 Claims, 5 Drawing Figures

U.S. Patent July 27, 1976 3,971,271
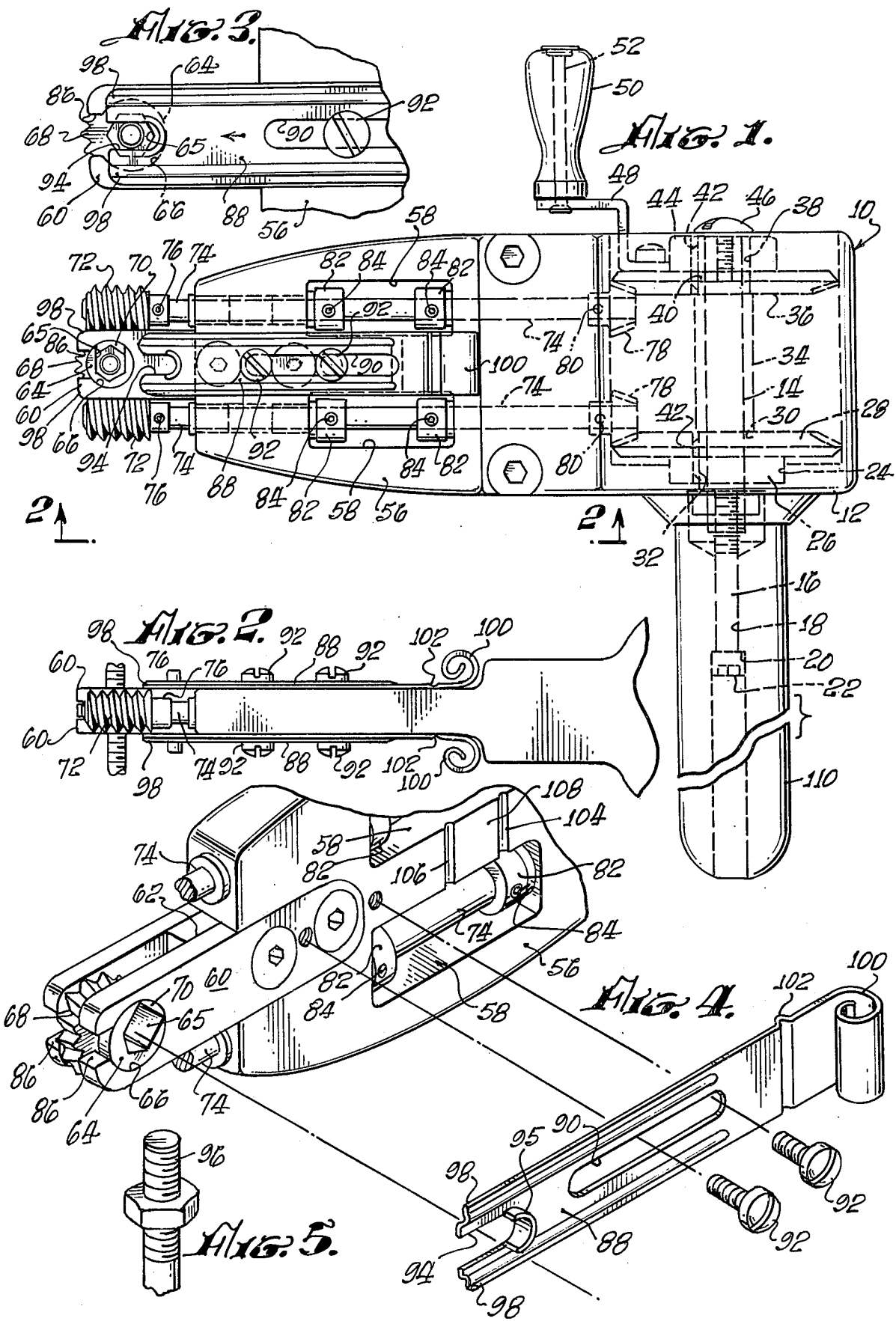

WRENCH FOR SURGICAL USE

BACKGROUND OF THE INVENTION

1. Field of the Invention

This invention relates generally to improvements in wrenches and relates more particularly to wrenches for surgical use in spinal fusion operations.

2. Description of the Prior Art.

As far as applicants are aware, there is no tool or wrench in the prior art adapted for surgical use. There are tools for use in plumbing and the like, but, these have disadvantages and are not adapted for use in surgery.

SUMMARY OF THE INVENTION

This invention is particularly adapted for surgical use in certain types of operations such as, for example, spinal fusion with internal fixation with threaded metallic rod.

The time in surgery is of extreme importance as infection and deterioration of bodily functions are directly tied to the duration in surgery.

In essence, the more rapid the fixation device can be put in place, the less time the patient is under anesthesia.

Our present device provides for rapid movement of the nut on the threaded rod so the nut does not have to be turned with a hand wrench as heretofor.

The device has a housing engaging driving gears operated by a crank. At one side of the housing, there is an extension from the free end of which there is a socket mounting projection with a slot extending inwardly from the free end and dividing the projection into two parts each of which has a hole therein, the holes being in alignment and receiving the socket. A socket has a flange disposed in the slot and said flange is toothed to form a worm wheel. At each side of the worm wheel is a worm gear carried by a shaft journaled in bushings in openings through the forward part of the extension. The shaft extending into the housing and carrying gears operated by respective beveled gears on a shaft driven by the crank. Collars on the shafts of the worm gears retain the worm gear shafts in operative position.

At each side of the extension, there is a slidable nut retainer having a forwardly opening notch at the free end adapted to receive an externally threaded rod having a nut thereon, the rod and nut being used in surgery as described above. The parts of the slidable nut retainer are adapted to overlap the nut when the slidable nut retainer is in the nut-holding position and there is an outwardly extending arcuate flange at the closed end of the notch for engagement with the rod when the nut retainer is in the operable or retaining position. The flange has sufficient height to span two or more threads of the screw to prevent entrance of the retainer between threads of the screw and binding. The nut retainers are movable to a position out of engagement with the nut and there is a ridge on the inner side of each retainer adapted to be received in corresponding notches at the limits of movement of said nut retainers. A handle connected to the housing is provided.

OBJECTS AND ADVANTAGES OF THE INVENTION

It is an object of the invention to provide a wrench for use in surgery such as in spinal fusion operations.

It is another object of the invention to provide a wrench of this character that effects rapid movement of a nut on a threaded rod or the like.

It is still another object of the invention to provide a wrench of this character that reduces the time involved in surgery so that the patient is under anesthesia a shorter time than heretofor.

A still further object of the invention is to provide a tool of this character wherein the nut is directly insertable into the socket of the tube at any position of the nut on the threaded rod.

A still further object of the invention is to provide a tool of this character having means for releasably holding the nut in place in the socket of the tool.

Another object of the invention is to provide means for releasably holding the nut in the socket of the tool, said means comprising a slidable member at each side of the tool, the members having notches in their forward free ends for reception of a threaded rod or screw and means for preventing the closed end of the notch from sliding into the space between threads.

Still another object of the invention is to provide an outwardly extending flange at the closed end of the notches for engagement with adjacent threads of the rod or screw to prevent binding of the mechanism.

A further object of the invention is to provide a tool of this character with which the nut may be driven in either direction whereby the nut may be tightened or loosened.

A still further object of the invention is to provide a wrench of this character having a direct positive drive.

The characteristics and advantages of the invention are further sufficiently referred to in connection with the following detailed description of the accompanying drawings, which represent one embodiment. After considering this example, skilled persons will understand that many variations may be made without departing from the principles disclosed and I contemplate the employment of any structures, arrangements or modes of operation that are properly within the scope of the appended claims.

BRIEF DESCRIPTION OF THE DRAWINGS

Referring to the drawings which are for illustrative purposes only:

FIG. 1 is a side elevational view of the tool embodying the present invention and having a portion of the housing broken away to show the interior arrangement of the driving gears;

FIG. 2 is a plane view as seen from line 2—2 of FIG. 1;

FIG. 3 is an enlarged plane view of the free end portion of the extension;

FIG. 4 is an exploded perspective view of the front portion of the extension of the device; and FIG. 5 is an enlarged view of a rod or shaft having a nut thereon for actuation by the socket of the tool.

DESCRIPTION OF THE PREFERRED EMBODIMENTS

Referring more particularly to the drawings, there is shown a wrench for surgical use having a hollow housing indicated generally at 10, said housing being generally cylindrical in shape and having a bottom wall 12 with a spindle or shaft 14. The lower end of said spindle being received in an opening closed at the bottom and secured by a screw 16; the screw 16 disposed in a bore 18. Bore 18 is counter sunk to provide a shoulder 20 against which the head 22 of screw 16 abuts to securely hold the spindle in place. There is an enlarged recess 24 in the bottom wall 12 for reception of a collar 26 integrated with a beveled gear 28. The latter has an axial opening 30 rotatably mounted in the housing. The size of the axial opening 30 of beveled gear 28 is substantially greater than the diameter of the spindle and there is a slot 32 which communicates with the axial opening 30. A sleeve 34 is rotatably mounted on the spindle and to the upper end of said sleeve, there is a second beveled gear 36 having an opening 38 disposed on a reduced diameter portion 40 of the sleeve. The reduced diameter portions of the sleeve have keys 42. The lower key fitting into the notch of the lower beveled gear and the upper key fitting into a notch provided therefore in the hub 44 of the upper beveled gear. A screw 46 secures the gears in proper relationship within the housing. Means for rotating the gears and sleeve comprises a crank 48 secured to the upper gear and having a handle 50 rotatable on a rivet pin 52.

At what may be considered the front or forward side of the housing, there is a radially extending block having a vertical slot therein for reception of the rear enlarged portion of an extension 56 which projects forwardly and has a pair of horizontally spaced parallel slots 58 and at the forward end of the extension, there are a pair of projection 60 which serve as a socket mount and which are spaced apart as at 62. At the forward end of the socket mount, there is a cross-bore defining aligned openings 66 for the opposite ends of a socket 64 which has a nut receiving opening 65 extending from one end of the socket to the other. The socket is provided with an externally toothed flange or a worm wheel 68.

As shown, the socket is for reception of a hexagonal nut although it may be of any other suitable shape for nuts of other shapes. Instead of having the usual six sides for the socket opening, the socket is slotted at 70 with the slot of the same width as two opposing parallel sides of the socket opening, said slot extending from the socket opening radially through the wall of the socket and worm wheel 68 which is disposed in the space 62 and is driven by a pair of worm gears 72, there being one worm gear at each side of the worm wheel. Worm gears 72 are attached to respective drive shafts 74 by means of set screws 76 and said shafts are rotatably disposed in shaft receiving parallel bores extending from the free end of the extension 56 and into the housing. The inner ends of said shafts have small beveled gears 78 attached thereto by any suitable means such as set screws 80, said small beveled gears 78 meshing respectively with the upper and lower gears 28 and 36 within the housing. Drive shafts 74 extend through the parallel slots 58 which are sufficiently large to accommodate collars 82 on the shafts adjacent the respective ends of the slots 58. The collars are secured to the shafts 74 by means of set screws 76 and said shafts are rotatably disposed in shaft receiving parallel bores extending from the free end of the extension 56 and into the housing. The inner ends of said shafts have small beveled gears 78 attached thereto by any suitable means such as set screws 80, said small beveled gears 78 meshing respectively with the upper and lower gears 28 and 36 within the housing. Drive shafts 74 extend through the parallel slots 58 which are sufficiently large to accommodate collars 82 on the shafts adjacent the respective ends of the slots 58. The collars are secured to the shafts 74 by means of set screws 84 and prevent the shafts from longitudinal movement.

The projections 60 each have a horizontal slot 86 said slots being aligned with each other and of substantially the same width as the slotted part of the socket so that when the slot of the socket is brought into register with the slots 86, a nut may be passed into or out of the socket through these slots.

By having the worm gears at diametrically opposite sides of the worm wheel, rotation of the worm wheel and socket is positively effected regardless of the position of the socket, since at least one worm gear is at all times in mesh with the worm wheel.

Means are provided for preventing the nut from sliding out laterally relative to the wrench and out of the nut receiving opening of the socket, there being one such means at each side of the extension and projections so a description of one such means will be sufficient since both are the same. This means comprises a retaining member 88 having a longitudinally extending slot 90 therein with a pair of screws 92 disposed in a slot for retaining the member 88 on the extension and its projection, said screws being spaced apart but the spacing is less than the length of the slot so that the screws serve as means for limiting movement of the member longitudinally. Member 88 has a notch 94 extending longitudinally from the free end thereof and of sufficient size to receive an externally threaded rod 96 therein. Notch 94 divides into two parts the front end portion of the nut retaining member 88, said parts being indicated at 98. Edge portions of the parts 98 overlap the nut receiving socket opening and prevent a nut in the socket from coming out of the adjacent end of the socket opening when the member 88 is at the forward nut retaining position. At the closed end of the notch, there is an arcuate outwardly extending flange 95 that is of a height to span at least two threads of the screw. This flange engages the screw when the retaining member is moved into the nut retaining position and prevents the inner or closed end of the notch from entering between threads of the screw and causing binding of the mechanism. It is to be understood that the tool is urged forwardly toward the screw sufficient to keep the nut in the socket and prevent it from inadvertently slipping out of the socket and into the notches 86, the flanges 95 preventing the retainers from entering between the threads of the screw and binding the mechanism.

Member 88 is adapted to be moved longitudinally to a nut release position there being a rolled part 100 for engagement with a finger or thumb of the operator for moving or sliding the nut retaining member between the nut retaining position and the nut releasing position. Member 88 also has a transverse ridge 102 stamped therein for release reception in cooperating grooves 104 and 106 in the wall 108 separating the slots 58. Grooves 104 and 106 are spaced apart so that the ridge 102 will enter one or the other when the member is at the release position or the nut retaining position so that the member 88 will be releasably retained in one or the other of these positions. Also, the ridge 102 will serve to increase the spring tension of the member 88 when moving on the wall 108 between the grooves 104 and 106 thus effecting a friction resistance to movement of the member 88 and prevent inadvertent movement of the member 88.

A handle 110 extends downwardly from the housing 10 for holding the tool when in use.

The invention and its attendant advantages will be understood from the foregoing description and it will be apparent that various changes may be made in the form, construction and arrangement of the parts without departing from the spirit or scope thereof or sacrificing its material advantages, the arrangement hereinbefore described being merely by way of example and we do not wish to be restricted to the specific form shown or uses mentioned except as defined in the accompanying claims.

We claim:

1. A wrench for surgical use, comprising:

a hollow housing;

an extension at one side of the housing;

said extension having a pair of shaft receiving parallel bores extending from the free end of the extension into the housing and spaced apart;

a pair of projections extending forwardly from the free end of the extension and spaced apart, there being aligned cross bores adjacent the ends of said projections and slots extending inwardly from the free ends of the parts into the respective cross bores, said slots being of less width than said cross bores, a socket rotatably disposed in said aligned bores, said socket having a nut receiving socket opening therein extending from one end of the socket to the other and having sides adapted to engage corresponding sides of nuts, said socket have a slot therein through which a nut is adapted to pass;

a worm wheel on the exterior of the socket and received in the space between the projections;

a pair of shafts rotatably disposed in the respective parallel bores in the extension;

a worm gear at the end of each of said shafts, said worm gears being at opposite sides of the worm wheel and operably engaging same;

gears within the housing secured to the respective shafts adjacent at inner ends, said gears being spaced apart;

a pair of interconnected gears within the housing engageable with the respective gears on the shafts;

means for operably rotating said interconnected gears;

a retaining member at each side of said extension and having a notch in the free end thereof, said retaining members being slidable between position whereat parts thereof at each side of the notch overlap the opening in the socket to prevent a nut in said socket from escaping laterally of the tool and a position whereat said retaining members are at an inoperative position.

2. The invention defined by claim 1, wherein there is means for holding the shaft in operative position.

3. The invention defined by claim 1, wherein the notches in the projections are of substantially the same width as the nut receiving opening in the socket and the slot in the socket extends through the worm wheel, the worm gears being so positioned that there will, at all times, be a driving connection between the worm wheel at least one of the worm gears.

4. The invention defined by claim 1, wherein there is a ridge on the inner side of each of the retaining members and there are notches in the extension for releasable retention of the retaining members, said notches being so located as to receive the ridge when the retaining members are respectively at the nut retaining position and at the inoperative position.

5. The invention defined by claim 1, wherein there is means on each retaining member for preventing said member from entering between threads and causing binding of the mechanism.

6. The invention defined by claim 5, wherein said means for preventing binding of the mechanism comprises an outwardly extending flange at the rear, closed end of the notch of each retaining member, said flange holding the inner end of the notch from entering between ribs of the screw when the retaining member is moved to its operative nut holding position.

7. The invention defined by claim 6, wherein the flange is arcuate and spans at least two ribs or threads of the screw.

* * * * *